United States Patent [19]
Kachel

[11] 3,970,928
[45] July 20, 1976

[54] ELECTRICAL APPARATUS FOR THE CALIBRATION OF EQUIPMENT USED IN THE MEASUREMENT OF PARTICLE VOLUME

[75] Inventor: Volker Kachel, Gauting, Germany

[73] Assignee: Max-Planck-Gesellschaft zur Forderung der Wissenschaften e.V., Gottingen, Germany

[22] Filed: Dec. 17, 1974

[21] Appl. No.: 533,658

[30] Foreign Application Priority Data
June 11, 1974 Germany............................ 2428082

[52] U.S. Cl. ........................................... 324/71 CP
[51] Int. Cl.² ........................................ G01N 27/04
[58] Field of Search ..................... 324/71 CP, 74; 235/92 PC

[56] References Cited
UNITED STATES PATENTS

| | | | |
|---|---|---|---|
| 2,656,508 | 10/1953 | Coulter | 324/71 CP |
| 3,670,150 | 6/1972 | Hogg et al. | 324/71 CP X |
| 3,745,455 | 7/1973 | Haigh | 324/71 CP |

Primary Examiner—Gerard R. Strecker
Attorney, Agent, or Firm—Edwin E. Greigg

[57] ABSTRACT

Calibration apparatus for use with particle volume measuring equipment using the Coulter process, which detects and analyzes the voltage pulses produced by particles passing a narrow aperture in which an electric field is maintained.

The calibration apparatus includes a calibration pulse generator with pulse-shaping circuitry which produces a sequence of calibration pulses, approximately trapezoidal in shape, which are introduced into the particle measurement path, in series with the measurement aperture traversed by the particles. The generator includes precision attenuation resistors for varying the amplitude of the calibration pulses.

The apparatus also provides for adjusting and maintaining a constant current through the measurement aperture and for amplifying the pulses produced by particles passing through the aperture whose amplitude is compared with the amplitude of the calibration pulses.

6 Claims, 4 Drawing Figures

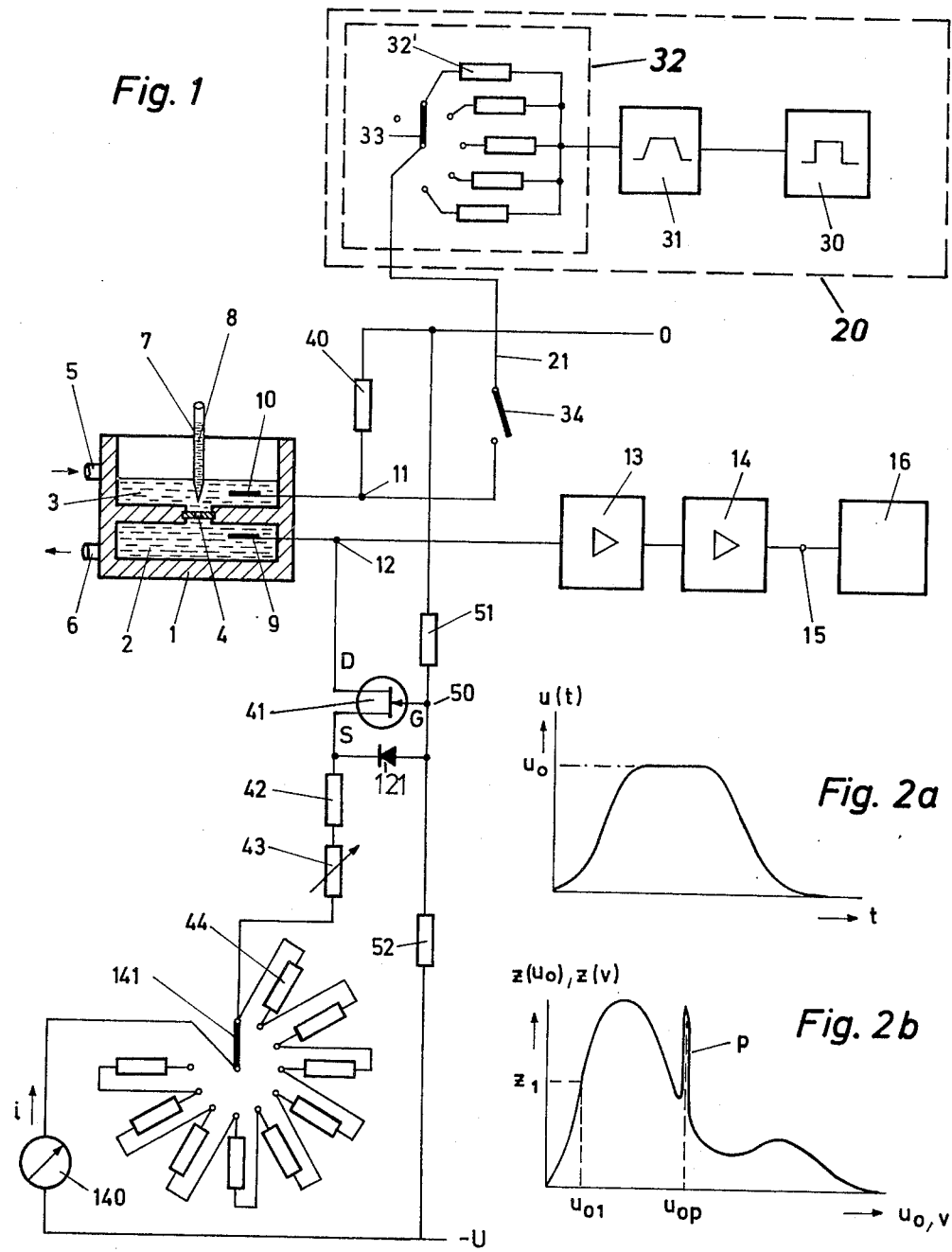

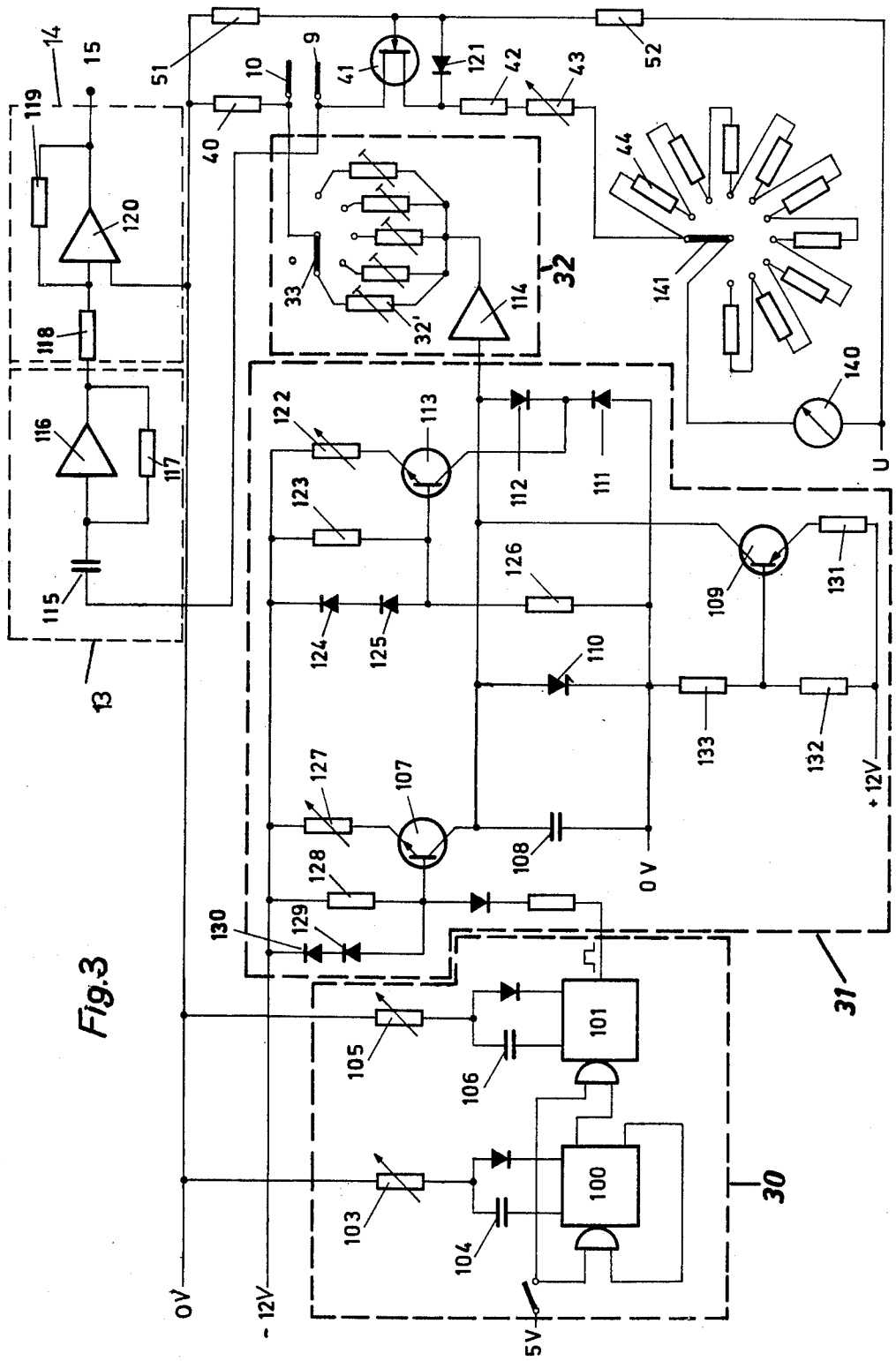

ELECTRICAL APPARATUS FOR THE CALIBRATION OF EQUIPMENT USED IN THE MEASUREMENT OF PARTICLE VOLUME

BACKGROUND OF THE INVENTION

The invention relates to an electrical circuit for the calibration of an apparatus (a measuring apparatus) which measures the volume of particles that flow through a measuring aperture in the stream of an electrolyte. Electrodes are disposed on both sides of the measuring aperture and the passage of particles through the aperture produces pulses which are evaluated in a data analysis unit. In the calibration process, a certain particle volume is associated arithmetically with the calibration pulses fed to the data analyzing unit.

Accordingly, the invention relates to an apparatus for the calibration of measuring apparatus for measuring particle volume according to the "Coulter" process, U.S. Pat. No. 2,656,508. Such apparatus is known in different embodiments, e.g., compare Kachel, Methods for the analysis and correction of apparatus-induced measuring errors in an electronic process for the determination of the size of particles according to Coulter, Berlin Dissertation 1972; Thom, "Comparative studies of electronic cell volume analysis", Published by A.E.G.-Telefunken, 1972; and DAS 1,806,512 and 2,013,799. Also known are circuits of the type described above for the calibration of such measuring apparatus (for instance Kachel, op.cit. page 55; Metzger, Valet, Kachel, Ruhenstroth-Bauer, "Blut," Volume 25, pages 179–184, 1972; Gutmann, "Elektromedizin" Volume 11, page 62, 196). Such apparatus or processes do not have the disadvantage of requiring calibration with particles of normalized size (Thom, Hampe, Sauerbrey, Z. ges. exp. Med., 151, pages 331–349, 1969) which is due to the fact that the accuracy of the data given by the manufacturer with respect to the dimensions of the normalized particles is not entirely reliable.

The known electrical calibration processes are based on the formula $$\frac{v}{V} = \frac{\Delta R}{R} \qquad (1)$$

according to which each artifically produced resistance change $\Delta R$ is associated, by means of a measuring aperture simulated by an electrical resistance, with that volume which a particle woul have if it produced the same resistance change when passing through the measuring aperture. In the formula:

$v$ is the volume of a particle passing through the measuring aperture $V$ is the volume of the measuring aperture (length $x$ cross-sectional area)

$R$ is the electrical resistance of the measuring aperture when no particle is passing through it and $\Delta R$ is the resistance change of the measuring aperture when a particle is passing through it.

When a particular volume $v$ is associated arithmetically with a particular resistance change $\Delta R$, consideration must also be given to a form factor (form of the particle) and a so-called capillary factor relating to the shape of the measuring aperture; however, the influence of these factors is applicable to the known apparatus in the same measure as for the apparatus according to the invention. For this reason, they need not be separately considered in the present connection.

The known electrical circuts (Kachel, Op. Cit. page 55) start by producing a resitance change $\Delta R$ at the input of the electronic portion of the measuring apparatus, i.e., the data analyzing apparatus. The value of this resistance change must be precisely defined with respect to the resistance of the actual measuring aperture and, for this reason, the resistance of the measuring aperture itself is simulated by another resistor. Thus, a resistance is applied to the input of the electronic part of the data analyzing unit which represents the resistance of the measuring aperture and this resistance is changed in a well-defined manner. Based on this resitance change and with the use of Formula (1), a particular particle volume is calculated and is associated with the voltage pulses received by the data analyzing unit and caused by the resistance change $\Delta R$.

A process of this type has several disadvantages: first of all, a simulation of the resistance of the measuring aperture is cumbersome because the true resistance of the measuring aperture must first be determined and simulated. During the calibration, the measuring aperture must be uncoupled from the data analyzing unit and the simulator must be attached. Now, from the point of circuit design, it is extremely difficult to produce resistance changes of approximately 0.1 to 0.01 percent in resistances of the order of magnitude of 10 kilo-ohms at repetition frequencies in the region of several kilohertz. When relays are used for switching in resistance changes, the resulting pulse shape is fixed as rectangular but this does not correspond to the true bell-shaped or trapezoidal form of the measuring pulses, which can lead to falsifications. When voltage-sensitive amplifiers are used in the analysis unit, it is necessary to simulate the resistance of the measuring aperture exactly and this is due to the fact that this resistance, together with the shielding capacitances, the further capacitances in the measuring system, as well as the capacitances of the input of the amplifier together form an RC member in the analysis unit which lengthens the rise time of the amplifier. In the case of very short pulses, this effect can even lead to a reduction of the amplitude and hence to a falsification of the calibration process, since the voltage pulses registered in the analysis unit must be identical during measuremment and calibraion. Furthermore, aside from this effect, deviations of the simulated resistance of the measuring aperture from its true resistance would be tolerable up to a limit of a few percent when using voltage-sensitive amplifiers, whereas, when using current-sensitive amplifiers, it is necessary to simulate the resistance of the measuring aperture with especially high precision because the magnitude of the input resistance directly influences the gain of such amplifiers.

OBJECT AND SUMMARY OF THE INVENTION

It is a principal object of the invention to provide a circuit of the above-described kind which does not have the cited disadvantages, i.e., in which there is no necessity for simulating the resistance of the measuring aperture by means of a precisely calibrated resistance.

This object is attained, according to the invention, by providing a calibration pulse generator which generates voltage pulses of predetermined amplitude serving as calibration pulses. These calibration pulses are fed to the measuring apparatus in series with the actual measurement path lying between the two electrodes and which includes the measuring aperture, in such a way that a volume calculated from the height of the calibration pulses may be associated with voltage pulses actually registered in the analysis unit.

In such a circuit, there is no necessity for simulating the measuring aperture since the calibration pules are directly fed into the actual measuring path which includes the measuring aperture. Similarly, there is no necessity for simulating a passage of a particle through the measuring aperture with the aid of a resistance change. For these reasons, the calibration process becomes considerably simpler and more precise. The generation of voltage pulses at the repetition frequencies which are likely to be used is possible with much less circuitry than would be necessary for producing the resistance changes required in the apparatus of the present state of the art. Furthermore, it is possible to make an actual measurement simultaneously with the calibration by voltage pulses, and, thus, any changes in the resistance of the measuring aperture, caused, for example, by exterior influences such as temperature, are continuously accounted for by a simultaneously occurring, new calibration.

An advantageous embodiment of the invention provides that the measurement of the voltage pulses fed in as calibration pulses is made by per se known current-sensitive amplifiers which act in principle as so-called operational amplifiers, and which exhibit a very high negative feedback. Their behavior is therefore characterized by the fact that only negligible voltage differences occur at their inputs and that, furthermore, the gain factor is proportional to the ratio of the negative feedback resistance to the input resistance. Such current-sensitive amplifiers may be used in a circuit according to the invention because, in contrast to the known circuits for calibrating the above-described measurement systems, no further change of the resistance occurs in the input circuit of the amplifier during calibration. Therefore, from this point of view, the dependence of the amplification factor on the resistance in the input circuit, which is a characteristic of current-sensitive amplifiers, does not have any effect on the calibration but the effect of this dependence is very advantageous when the input resistance, i.e., the actual resistance of the measuring aperture, changes due to other circumstances than the passage of a particle, for example, due to temperature fluctuations or due to use of an electrolyte of different conductivity, etc. In that case, this resistance change in the input circuit of the amplifier results in a compensating change of the gain factor of the current-sensitive amplifier.

The above-cited property of the current-sensitive amplifier, namely that, due to its high open-loop gain and its high negative feedback, practically no voltage differences occur at its input, also leads to the fact that extraneous and disturbing capacitances no longer play a role.

A further advantageous embodiment of the invention provides that the calibration pulse generator includes a pulse-shaping circuit which imparts to the calibration pulse a shape similar to the shape of the pulse which occurs when a particle passes the measuring aperture.

The invention wll be better understood as well as further objects and advantages thereof will become more apparent, from the ensuing detailed specification of exemplary embodiments taken in conjunction with the drawing.

BRIEF DESCRIPTION OF THE DRAWING

FIG. 1 is a schematic representation of an exemplary embodiment of the invention;

FIG. 2a is the typical form of a pulse occurring when a particle passes a measuring aperture;

FIG. 2b is a volume distribution curve such as produced by processing several pulses of the type shown in FIG. 2a; and FIG. 3 is a more detailed schematic diagram of the circuit shown in FIG. 1.

DESCRIPTION OF THE PREFERRED EMBODIMENT

FIG. 1 depicts a container 1 having two chambers 2 and 3 which communicate via a measuring aperture 4. Chamber 3 is supplied through a line 5 with particle-free electrolyte which flows through the measuring aperture 4 into chamber 2 and thence is aspirated through a line 6. A suspension 8 of particles whose properties are to be measured is fed from a supply capillary tube 7 into the narrowing stream of the particle-free electrolyte. The continuously narrowing thread of particles flows to the measuring aperture 4, where they pass sequentially through the measuring aperture 4. During their passage, they cause a shift of the electric field lines maintained within the measuring aperture 4 and, hence, cause an effective resistance change which, in turn, causes a voltage pulse to occur between the electrodes 9 and 10 when an electric current is flowing. This voltage pulse appears at the connectors 11 and 12 and its amplitude and time-behavior contain information regarding the volume and/or other parameters (for example, the shape) of the particle which has passed through the measuring aperture 4 and which has caused this resistance change. The voltage pulse is picked off at the connector 12, is amplified in a preamplifier 13 and a post amplifier 14 and is available for further analysis at a point 15. This analysis is indicated schematically in FIG. 1 by an analysis or processing nut 16. The analysis or processing which may take place in the unit 16 can consist, for example, of pulse-height classification from which a volume distribution curve can be derived due to the functional relationship between the pulse height and volume. A typical time behavior of such a voltage pulse $u(t)$ as it occurs at the junction 12 or (after amplification) at the junction 15 is shown in FIG. 2a. The result of analyzing several such voltage pulses produced by several particles in a classifying device (classification according to pulse height $u_o$) is shown in the curve of FIG. 2b. From such a curve it may be seen how many ($z$) particles have produced a voltage pulse of a particular height $u_o$ (for example $z_1$ particles have produced a voltage pulse of a pulse height $u_{o1}$). Now, if a particular particle volume can be associatd with a particular pulse height $u_o$, then FIG. 2b represents the volume distribution curve of a certain quantity of particles, namely, that quantity of particles which is contained in the particle suspension 8. A calibration of this functional association is made as follows: Voltage pulses of pulse height $u_{op}$ are produced at the junction 12 or, after amplification, at the connection 15 and they generate the peak $p$ in FIG. 2b. Now, if it is possible to associate the value $u_{op}$, which coincides with the peak $p$, with a predetermined particle volume, based on the manner in which it is produced, then the curve in FIG. 2b may be calibrated as a volume distribution curve $z(v)$.

In the formula $$\frac{v}{V} = \frac{\Delta R}{R} \quad (1)$$

one substitutes the geometry of the measuring aperture ($l$ is the length of the measuring aperture, $r$ is the radius of the measuring aperture) and also the electrical properties of the particle ($\sigma$ is the conductivity, $\rho = 1/\sigma$), one obtains $$v = \Delta R \cdot \frac{\pi^2 r^4}{\rho} \quad (2)$$

If the right side of this expression is multiplied and divided by the measuring current $i$, one obtains $$v = \Delta R \cdot i \cdot \frac{\pi^2 r^4}{\rho \cdot i} = \frac{\Delta u \, \pi^2 r^4}{\rho \cdot i} \quad (3)$$

Thus, if the measuring current $i$, the radius $r$ of the measuring aperture 4 and the conductivity $\sigma$ of the particles are all known, then a single volume $v$ may be unambiguously associated with each pulse height $\Delta u$ (as has been mentioned in the beginning, a form factor accounting for the form of the particles and a capillary factor accounting for the shape of the measuring aperture must be considered in this formula, as is known in principle).

As has already been explained, in the known calibration processes, a voltage pulse was produced at the connections 12 or 15 by separating the measuring chamber 1 from the connections 11 and 12. In its place, the calibration circuit was then connected to them with simulated the previously exactly determined resistance of the measuring aperture 4 by means of a precision resistor. Further resistors were then connected to this resistor so that a known resistance change $\Delta R$ was produced. The voltage pulses produced thereby at the connections 12 or 15 and the location of their occurrence in the distribution curve according to FIG. 2b were then associated with a particular volume $v$ by calculation and the use of formula (1).

By contrast, in the circuit according to the invention shown in FIG. 1, the measuring path lying between the electrodes 9 and 10, which also includes the measuring aperture 4, is connected between a potential $-U$ and a ground connection at a potential 0, in series with, on the one hand, a resistor 40 which has a relatively low value of resistance with respect to the resistance of the measuring aperture 4 but has relatively high precision (for example 1 ohm with a precision of 1%) and, on the other hand, with resistors 42, 43, 44 as well as with a current measuring device 140 which indicates the measuring current $i$ flowing through the measuring path. The magnitude of the measuring current $i$ can be adjusted by appropriately switching in or out individual ones of resistors 44 with the aid of switch 141. This adjustable measuring current is kept constant by a series connection of the drain-to-source path (a connection made between the drain D and source S) of a field effect transistor 41 whose gate G is connected to the point 50 of a voltage divider formed by the resistors 51 and 52 and thus is held at a constant potential. In this circuit, the measuring current, which is equal to the drain current, depends in practice only on the gate voltage (the voltage at point 50) and on the resistors 42, 43, 44 but does not depend on the resistance of the measuring aperture 4.

In an exemplary embodiment of the invention, the potential $-U$ was made equal to $-107$ volt and the voltage divider formed by resistors 51 and 52 was so dimensioned that a gate voltage of approximately 40 volts was present at the point 50. This insured, on the one hand, that sufficient control remained over the voltage across the measuring path, i.e., between the electrodes 9 and 10, and, on the other hand, eliminated any influence of voltage fluctuations as between the gate G and the source connection S, due, for example, to temperature fluctuations, etc. The diode 121 in parallel with the source-gate path prevents a substantial drop of the voltage at the source connection S below the voltage present at gate G when the electrode 9 or 10 are disconnected from the connection points 11 or 12.

For purposes of calibration, voltage calibration pulses from a calibration pulse generator 20 are introduced into the measuring path at the connection 11, through a line 21 and a switch 34. The calibration pulse generator 20 includes a square wave generator 30 feeding into a pulse shaping circuit 31 and, in series therewith, a network 32 formed from several resistors 32'. A switch 33 permits the selective contact with diffeent resistors 32, i.e., with different voltages. The pulse forming circuit 31 transforms the input pulses into pulses with a well-defined height and a shape which represents an adaptation to the shape of those pulses which are produced when particles pass through the measuring aperture 4 (compare FIG. 2a). A useable approximation is represented by the trapezoidal form of the calibration pulses as is indicated schematically in the box 31 representing the pulse shaping circuit.

The resistances 32' are so large with respect to the resistance 40, which is, for example, 1 ohm (compare above) that, in practice, a well-defined current is produced by the calibration pulse generator 20 and flows through the resistance 32' and the resistance 40. This current is superimposed on the measuring current $i$ and is independent of the potential which the measuring current $i$ produces at the connection 11. For example, if the voltage at the input of the network 32 is 8.2 volts, and if the resistance 32' is 8.2 kilo-ohms and if, furthermore, the condition that the resistance 40 is small as compared with resistance 32' is fulfilled, then a current of 1 milliampere flows through the resistance 40 and produces a voltage drop of 1 millivolt across this resistance 40. Since the resistance 40 is also small as compared with the resistance of the measuring aperture, this voltage pulse with an amplitude of 1 mV also appears at the connection 12 and thus is introduced in series with the measuring path between the electrodes 9 and 10. This voltage pulse is the calibration pulse.

Now, if switch 34 is closed, and if several sequential calibration pulses of equal amplitude are introduced, they produce voltage pulses of amplitude $u_{op}$ at the connection 15. These pulses are registered in the analysis unit 16 and a certain particle volume $v$ may be associated with them by calculation according to formula (3). This is the volume of a particle which would produce a voltage pulse of the same amplitude if it had passed through the measuring aperture 4. A sufficient number of such equal calibration pulses produces a peak $p$ in the distribution curve of FIG. 2b with whose position in the curve the calibrated value of the volume is associated. In this way, a distribution curve like that in FIG. 2b is calibrated as a volume distribution curve.

As has already been emphasized above, the calibration does not take place over a simulated measuring path but over the actual measuring path formed by the electrolyte between the two electrodes 9 and 10 and it is therefore determined by the actual properties of the measuring aperture 4. The voltage pulse which is used for calibration is no longer produced by a resistance change in a simulated measuring path but rather is produced by introduction of voltage pulses of known amplitude into the actual measuring path.

FIG. 3 is a detailed schematic diagram of the preferred exemplary embodiment according to the invention. Identical elements retain the same reference numerals as they had in FIG. 1.

The square wave generator 30 is formed by a square wave oscillator consisting of a dual monostable multivibrator constructed from a dual TTL integrated circuit (e.g. integrated circuit type 74123, manufacturer Texas Instruments Co.) 100 and 101. Its frequency is determined by the resistor 103 and the capacitor 104 and the pulse width is determined by the resistor 105 and the capacitor 106. The rectangular pulse delivered by the square pulse generator 30 (shown at the output of the TTL-IC 100 in FIG. 2), has the effect of making the transistor 107 conductive. The two diodes 129, 130, the resistor 128 and the variable resistor 126 together represents a first constant-current circuit which keeps the current which is switched on by transistor 107 at a precisely determined value which may be set by means of the resistor 127. This current is divided into two parts; one part charges the capacitor 108 whose other side is connected to a zero volt potential, whereas the other half of the current flows through a transistor 109 and this part of the current is held constant by resistors 131, 132 and 133 which, together with the transistor 109, form a second constant-current circuit. When the charge on the capacitor 108 is such that its voltage equals the breakdown voltage of the Zener diode 110, no further charging takes place and the charge of the capacitor 108 remains at a certain level. When the rectangular pulse at the input of the pulse shaping circuit 31 drops back to the low value, the transistor 107 shuts off and the capacitor 108 discharges, again at constant current, through the transistor 109 belonging to the second constant-current circuit. This discharging process is interrupted when the side of the capacitor 108 connected to the collector of transistor 107 is exactly at zero potential. This purpose is served by the transistor 113, the variable resistor 122, the resistor 123 and the two diodes 124 and 125, forming a third constant current circuit. At the instant at which the potential of that side of the capacitor 108 connected to the collector of the transistor 107 becomes zero, the diode 112 becomes conductive. From this point on, the constant current flowing through the transistor 109 no longer flows (as a discharge current) out of capacitor 108 but rather flows through the diode 112 and the transistor 113.

In order to bring the potential on both sides of the capacitor 108 exactly to zero volts, the transistor 113 is so adjusted that the current flowing through it is twice as large as the current flowing through the transistor 109, where the additional current is pulled by the transistor 113 through the diode 111 from its zero volt connection. If both the diodes 111 and 112 have the same conduction voltage, and if half the current flowing through the transistor 113 flows through the diode 111, whereas the other half flows through the diode 112 and the transistor 109, then it is guaranteed that both sides of the capacitor 108 will be at exactly the same potential, namely, at zero volts. As long as the diode 112 does not conduct, i.e., as long as the capacitor 108 has not been discharged to zero volts, the entire current flowing through the transistor 113 flows through diode 111.

This guarantees that, at the onset of the rectangular pulse, charging occurs at constant current and that, when the rectangular pulse is terminated, the discharge process also occurs at constant current. Hence, the input of the network 132 is provided with a voltage pulse of trapezoidal shape which therefore substantially approximates the pulse shape shown in FIG. 2b.

The input of the network 32 is provided with an impedance transformer 114 (integrated circuit LM 302 of National Semiconductor). From its output, the voltage pulse goes, depending on the position of switch 33, to one of the resistors 32' and hence to the connection 11 and to the resistor 40. The resistances 32' are adjusted to a precision of 1% in such a way that calibration pulses with an amplitude varying between 0.5 and 5 millivolts can be produced at the connection 11.

The voltage pulse then proceeds from the connection 12 to the preamplifier 13 and the post-amplifier 14 whose output appears at the connection 15 to which an analysis unit 16 is connected (compare FIG. 1).

In principle, the amplifiers may be either voltage- or current-sensitive amplifiers. It is possible to use current-sensitive amplifiers because the resistance connected to the input of the amplifier remains constant during calibration. Because of its high negative feedback, only a practically negligible potential difference occurs at the input of such an amplifier so that stray capacitances remain advantageously without effect. A more detailed description of such amplifiers is unnecessry because current-sensitive amplifiers are known to the specialist. They are indicated in FIG. 3 by two amplifiers 116 and 120 with high open-loop gain and high feedback through the feedback resistors 119, 117 and include an input capacitor 115 and input resistor 118.

What is claimed is:

1. In an electrical apparatus for calibration of measurement equipment for measuring the volume of particles, which includes two chambers filled with liquid electrolyte which communicate through a measurement aperture, and which further includes two electrodes located on opposite sides of the aperture, by which a current can be passed through the aperture, and which further includes means for introducing particles into the first of said two chambers, said particles passing through said measurement aperture, thereby generating voltage pulses across the electrodes, said apparatus further including a processing and analysis unit for processing and analyzing said voltage pulses, and including means for producing calibration voltage pulses which are used by said processing and analyzing unit to associate a certain particle volume with a certain voltage pulse amplitude, the improvement comprising:

a resistor which is positioned in the electrical path in series with said measurement aperture, said resistor having an ohmic resistance which is small with respect to the ohmic resistance of said measurement aperture; and a calibration pulse generator, for producing calibration voltage pulses of adjustable amplitude, said calibration voltage pulses being introduced into the electrical path formed between said resistor and said measurement aperture, thereby applying the calibration voltage pulses essentially across the electrodes, said calibration pulses also being fed to the processing and analyzing unit, in which a numerical volume derived by calculation and theory from said calibration voltage pulses is associated with the voltage pulses received by said processing and analysis unit.

2. An electrical apparatus as defined in claim 1, the improvement further comprising:

at least one current-sensitive amplifier for amplifying said calibration voltage pulses after their passage over the electrical path formed between said two electrodes.

3. An improved apparatus as defined in claim 1, wherein said calibration pulse generator includes a plurality of resistors, selective ones of said resistors being capable of being connected in series with the output of said calibration pulse generator to adjust the amplitude of said calibration voltage pulses.

4. An improved apparatus as defined in claim 1, wherein said calibration pulse generator further includes:

an oscillator for producing rectangular pulses; and pulse-shaping circuitry, for transforming said rectangular pulses into calibration pulses whose shape conforms approximately to the shape of the voltage pulses which occur when a particle passes through said measurement aperture.

5. An apparatus as defined in claim 4, wherein said pulse-shaping circuitry includes:

a first constant current source, switched on by one of said rectangular pulses;

a capacitor, capable of being charged by said first constant current source;

voltage limiting means, for limiting the voltage impressed on said capacitor by charging;

a second constant current source, connected to said capacitor, for discharging said capacitor when said rectangular pulse has turned off said first constant current source;

a first diode, connected in series with said second constant current source; and a third constant current source, connected in series with said first diode; whereby, after said capacitor has discharged to zero potential, said first diode becomes conductive and the current delivered by said second constant current source flows through said first diode and through said third constant current source.

6. An apparatus as defined in claim 5, said pulse-shaping circuitry further including:

a second diode, connected to the junction of said first diode and said third constant current source and to the side of said capacitor connected to zero potential, for compensating the voltage drop across said first diode with respect to the side of said capacitor connected to said first constant current source and produced by the current flowing through said second and said third constant current sources after the discharge of said capacitor.

* * * * *

UNITED STATES PATENT OFFICE
CERTIFICATE OF CORRECTION

Patent No. 3,970,928    Dated July 20, 1976

Inventor(s) VOLKER KACHEL

It is certified that error appears in the above-identified patent and that said Letters Patent are hereby corrected as shown below:

Column 1, line 34, "196" should be --1966--;

line 52, "woul" should be --would--.

Column 2, line 48, "calibraion" should be --calibration--.

Column 4, line 42, "nut" should be --unit--.

Column 5, line 3, "In the formula" should be --If in the formula--;

line 38, "with" should be --which--;

line 52, "a" should be deleted.

Column 6, line 29, "diffeent" should be --different--.

Column 7, line 31, "represents" should be --represent--.

Signed and Sealed this

Fifth Day of October 1976

[SEAL]

Attest:

RUTH C. MASON
*Attesting Officer*

C. MARSHALL DANN
*Commissioner of Patents and Trademarks*